United States Patent [19]

McRae

[11] Patent Number: Plant 6,521

[45] Date of Patent: Jan. 10, 1989

[54] LILY NAMED SUMMER PIXIE

[75] Inventor: Edward A. McRae, Boring, Oreg.

[73] Assignee: Melridge, Inc., Aurora, Oreg.

[21] Appl. No.: 6,024

[22] Filed: Jan. 22, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant of short, two to two and one-half foot stature, bearing large clusters of flowers of medium to large size and particularly characterized by their rich orange coloration accented by a golden orange midrib. The short stature of the plant, its short but full leaves, and the long persistence of its blooms make it especially suitable as a pot plant variety. The color pattern and silhouette of this plant are completely new in the upright Asiatic divisions of lilies suited to forcing and to mass commercial cultivation.

This plant is highly resistant to disease and shows high tolerance of virus, making it an excellent garden plant. The bulbs of this plant may be precooled and forced throughout the year for pot plant production and the clone is vigorous and is a good grower and propagator.

1 Drawing Sheet

BACKGROUND OF THE NEW PLANT

This new variety of lily plant originated as a seedling selected from a group of seedlings planted at Sandy, Oreg., and resulting from my crossing of the clonal cultivar 'Charisma' U.S. Plant Pat. No. 4,180 as the seed parent with the clonal cultivar 'Sunray' (unpatented) as the pollen parent. The object of this crossing was the production of lilies in shades of orange and yellow well suited to forcing for pot plant production out of season, heretofore unknown in the lily breeding art, and this particular seedling was selected for propagation and test because of its short stature and the rich coloration of its blooms which is accented by golden orange midribs and an attractive ring of spots encircling the center of the flower, a feature unique in this type of lily. This new plant was propagated by me and under my direction at Sandy, Oreg., through several successive generations by bulb scale propagation and natural propagation from bulblets and I have found that this new variety remains short and is not overly susceptible to bud abortion when forced into flower out of season as a pot plant. In addition, I have found that the clone possesses to a high degree the desirable characteristics of hybrid vigor, great hardiness and disease resistance; and the asexual propagation of this new variety by me and under my direction at Sandy, Oreg., has demonstrated that the novel characteristics of this new plant hold true from generation to generation and appear to be firmly fixed.

Working with this new plant at Sandy, Oreg., I have found that this variety is well suited to forcing out of season when the bulbs are dug at the appropriate time and properly precooled; October-dug bulbs, properly precooled and potted in January, will flower under glass in Oregon, with no supplementary lighting and at moderate greenhouse temperatures, in an average of sixty-five to seventy-five days.

DESCRIPTION OF THE DRAWING

My new hybrid lily cultivar is illustrated by the accompanying full color photographic drawing, which shows several buds in flower and in particular a three-fourths face view of a fully developed bloom, the colors shown being as nearly true to those herein specified as is reasonably possible to obtain by conventional professional photographic procedures.

DESCRIPTION OF THE NEW PLANT

The following is a detailed description of my hybrid lily cultivar based upon observations of plants grown at Sandy, Oreg., during the middle of 1986, the color designations being according to The R.H.S. Colour Chart published by The Royal Horticultural Society of London, England, in 1966.

THE PLANT

Origin: Seedling.

Parentage:

- *Seed parent.*—Lilium 'Charisma' U.S. Plant Pat. No. 4,180.
- *Pollen parent.*—Lilium 'Sunray' (unpatented).

Classification:

- *Botanic.*—Division I-A, upright Asiatic hybrid lily (Horticultural Classification of Lilies, Royal Horticultural Society of London).
- *Commercial.*—Hybrid Lilium Clone.

Form: Single stem, erect and stately.

Height: About 40 to 60 cm. on stems produced by glasshouse forcing of bulbs of about 15 to 18 cm. in circumference, provided light levels are adequate; low light levels may cause "stretching".

Growth: Vigorous and upright.

Foliage:

- *Quantity.*—Abundant.
- *Size of leaf.*—About 5 to 8 cm. long and about 1 cm. wide.
- *Shape of leaf.*—Lanceolate with acuminate tip and entire margins.
- *Texture.*—Leathery.
- *Aspect.*—Glossy and lightly pubescent along the margins.
- *Color.*—Dark green, somewhat lighter on the bottom side.

The bulb:

- *Size.*—Various, ranging to about 25 cm. in circumference as commercially used.
- *Color.*—White.

THE BUD

Form: Long ovoid with obtuse tip.

Size: About 8 to 9 cm. long and about 5 cm. in circumference just prior to opening.

Opening rate: The bud opens slowly taking about one hour in response to morning light.

Color: Buff orange just prior to opening and as the tepals begin to unfurl.

Peduncle:

*Length.*—About 4 to 6 cm. in average. The peduncle may elongate if light levels are too low or if the bulbs have been improperly stored prior to forcing.

*Color.*—Dark green with deep plum overlay.

THE FLOWER

Blooming habit: Once annually and profusely in midseason.

Size: About 13 to 15 cm. in diameter, in average.

Borne: In a single compact raceme having 5 to 8 buds from a bulb about 12 to 16 cm. in circumference.

Shape: Cup shaped when first opened and flattening as the tepals recurve during the second day.

Tepalage: Normal, with six imbricated tepals in hexagonal arrangement.

*Color.*—The base color is a rich orange, 30C, and there is a stripe of golden orange, 23A, about 1 cm. wide and extending for about 2 cm. from the nectaries along the midrib of each tepal. Under certain conditions of light and temperature, the base of the golden orange stripe may be lightly brushed with a soft purple-red marking, 47C, about 5 mm. long and 2 to 4 mm. wide. The border of the nectary furrows is white and lightly pubescent.

*Spotting.*—The base third of each tepal is marked with small magenta-purple spots just about the nectaries which, with the adjoining tepals, form a ring surrounding the center of the bloom.

*Aspect.*—Shiny.

*Longevity.*—The tepals stay on the stems about three weeks.

Pedicel:

*Length.*—About 5 to 10 cm., in average.

*Color.*—Dark green with plum overlay.

*Character.*—Sturdy and ascending up to about sixty degrees from the horizontal. Secondary buds occur very rarely.

Color changes: The flower color deepens to 30B-C along the midrib as the flower ages, if the light levels are adequate for cut flower and pot plant maintenance.

Disease resistance: The flower and plant are resistant to disease; in particular, they are resistant to Fusarium bulb rot and Botritis blight.

Lasting quality: The flower is long lasting, both on the plant and as a cut flower.

REPRODUCTIVE ORGANS

Stamens:

*Number.*—Six, with arrangement typical of genus Lilium.

*Anthers.*—Color: Soft orange, 26B.

*Filaments.*—Length: About 5 cm.

*Pollen (anthers dehisced).*—Color — Greyed orange, 169B.

Pistil:

*Number.*—One.

*Style.*—About 5 cm. long.

*Stigma.*—Soft green with deep plum overlay.

Character of ovary: The ovary is characteristic of genus Lilium.

THE FRUIT

Fertility: The fruit is fertile.

Shape: Ovoid.

Color at maturity: Soft brown, sometimes overlaid with soft plum.

This new lily variety most closely resembles the variety 'Charisma' but differs in having spotted flowers, a much higher bud count and shorter leaves. The new plant is also more reliable and uniform in its forcing performance than 'Charisma' and the short stemmed, short leaved, upright flowering silhouette is ideal for pot plant culture, these characteristics of form and color pattern being unique among Asiatic hybrid lilies suited to forcing and to mass commercial cultivation.

I claim:

1. A new and distinctive variety of Asiatic hybrid lily, substantially as herein shown and described, characterized by its rich orange flowers accented by golden orange midribs and a decorative ring of spots encircling the center of the flowers; the excellence of the flower form; and its versatility both as a garden plant and as a pot plant variety well suited to forcing into flower out of season from properly precooled bulbs.

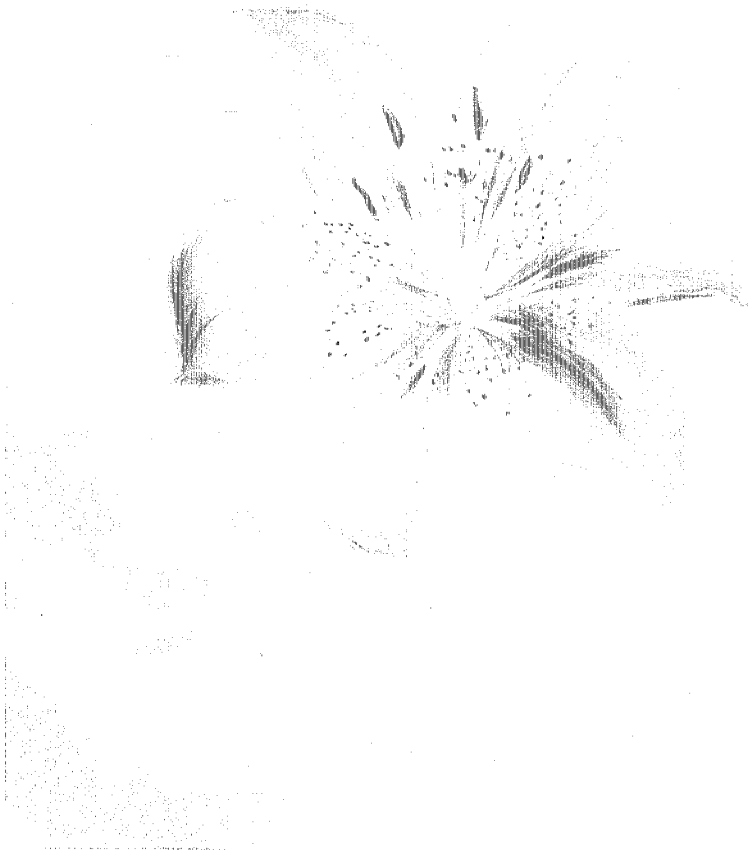

* * * * *